United States Patent
Jensen et al.

(10) Patent No.: US 9,591,411 B2
(45) Date of Patent: Mar. 7, 2017

(54) SELF-CALIBRATION OF MULTI-MICROPHONE NOISE REDUCTION SYSTEM FOR HEARING ASSISTANCE DEVICES USING AN AUXILIARY DEVICE

(71) Applicant: Oticon A/S, Smørum (DK)

(72) Inventors: Jesper Jensen, Smørum (DK); Michael Syskind Pedersen, Smørum (DK)

(73) Assignee: OTICON A/S, Smorum (DK)

( * ) Notice: Subject to any disclaimer, the term of this patent is extended or adjusted under 35 U.S.C. 154(b) by 0 days.

(21) Appl. No.: 14/678,179

(22) Filed: Apr. 3, 2015

(65) Prior Publication Data

US 2015/0289064 A1    Oct. 8, 2015

(30) Foreign Application Priority Data

Apr. 4, 2014   (EP) .................................... 14163499

(51) Int. Cl.
  *H04R 25/00*   (2006.01)
  *A61N 1/36*    (2006.01)
  *H04R 3/00*    (2006.01)

(52) U.S. Cl.
  CPC ......... *H04R 25/50* (2013.01); *A61N 1/36032* (2013.01); *H04R 3/002* (2013.01);
  (Continued)

(58) Field of Classification Search
  CPC .......... H04R 1/40; H04R 1/406; H04R 3/005; H04R 3/12; H04R 5/027; H04R 5/04;
  (Continued)

(56) References Cited

U.S. PATENT DOCUMENTS 7,327,852 B2 *  2/2008  Ruwisch ................. G10L 21/02
                                                   381/356
7,639,828 B2 * 12/2009  Platz .................... H04R 25/558
                                                   381/312

(Continued)

FOREIGN PATENT DOCUMENTS

DE     20 2006 002 322 U1    3/2007

OTHER PUBLICATIONS

Kjems et al., "Maximum Likelihood Based Noise Covariance Matrix Estimation for Multi-Microphone Speech Enhancement", 20th European Signal Processing Conference, 2012, pp. 295-299.

(Continued)

*Primary Examiner* — Curtis Kuntz
*Assistant Examiner* — Joshua Kaufman
(74) *Attorney, Agent, or Firm* — Birch, Stewart, Kolasch & Birch, LLP

(57) ABSTRACT

A hearing assistance system calibrates a noise reduction system of a hearing assistance device. The system comprises a hearing assistance device, and an auxiliary device. The hearing assistance device comprises a multitude of input units, and a multi-channel beamformer filtering unit configured to determine filter weights for a beamformed signal. The system further comprises a user interface for activating a calibration mode. The auxiliary device comprises an output transducer for converting an electric calibration signal to an acoustic calibration sound signal. The system is configured to estimate a look vector for a target signal originating from a target signal source located at a specific location relative to the user based on the acoustic calibration sound signal.

19 Claims, 7 Drawing Sheets

(52) U.S. Cl.
CPC ........... *H04R 25/30* (2013.01); *H04R 25/407* (2013.01); *H04R 25/558* (2013.01); *H04R 2225/41* (2013.01); *H04R 2430/23* (2013.01)

(58) Field of Classification Search
CPC ....... H04R 25/30; H04R 25/40–25/505; H04R 25/552–25/558; H04R 2201/40–2201/405; H04R 2430/20–2430/25; H04R 2499/11
See application file for complete search history.

(56) References Cited

U.S. PATENT DOCUMENTS

| | | | | |
|---|---|---|---|---|
| 7,864,968 | B2* | 1/2011 | Kulkarni | A61N 1/36032 381/60 |
| 7,995,771 | B1* | 8/2011 | Faltys | H04R 25/407 381/313 |
| 9,049,525 | B2* | 6/2015 | Nielsen | H04R 25/554 |
| 2004/0190737 | A1* | 9/2004 | Kuhnel | H04R 25/305 381/312 |
| 2004/0190739 | A1* | 9/2004 | Bachler | H04R 25/305 381/314 |
| 2006/0204024 | A1* | 9/2006 | Eicher | H04R 25/558 381/315 |
| 2007/0282393 | A1* | 12/2007 | Marquis | H04R 25/30 607/55 |
| 2008/0101635 | A1* | 5/2008 | Dijkstra | H04R 25/30 381/315 |
| 2011/0026725 | A1* | 2/2011 | Kunzle | G10L 21/0208 381/71.11 |
| 2011/0064232 | A1* | 3/2011 | Ruwisch | H04M 1/24 381/59 |
| 2011/0103626 | A1* | 5/2011 | Bisgaard | H04R 3/005 381/313 |
| 2011/0255725 | A1 | 10/2011 | Faltys et al. | |
| 2012/0250916 | A1* | 10/2012 | Hain | H04R 25/407 381/313 |
| 2013/0094664 | A1* | 4/2013 | Ruwisch | H04R 3/005 381/92 |
| 2013/0343585 | A1* | 12/2013 | Bennett | H04R 25/554 381/315 |
| 2014/0056435 | A1* | 2/2014 | Kjems | H04M 9/082 381/66 |
| 2014/0146987 | A1* | 5/2014 | Pontoppidan | H04R 25/30 381/314 |
| 2014/0176297 | A1* | 6/2014 | Mulder | G09B 21/009 340/4.14 |
| 2014/0233774 | A1* | 8/2014 | Kim | H04R 25/30 381/315 |
| 2015/0023536 | A1* | 1/2015 | Scheller | H04R 25/30 381/315 |
| 2015/0110310 | A1* | 4/2015 | Minnaar | H04R 5/00 381/307 |
| 2015/0125015 | A1* | 5/2015 | Van Der Werf | H04F 1/1091 381/318 |
| 2015/0172814 | A1* | 6/2015 | Usher | H04R 3/005 381/92 |
| 2015/0213811 | A1* | 7/2015 | Elko | H04R 3/005 381/92 |
| 2015/0256942 | A1* | 9/2015 | Kinsbergen | H04R 25/30 381/313 |
| 2015/0256956 | A1* | 9/2015 | Jensen | H04R 25/30 381/56 |
| 2015/0289063 | A1* | 10/2015 | Ma | H04R 25/50 381/321 |
| 2015/0289064 | A1* | 10/2015 | Jensen | A61N 1/36032 381/317 |

OTHER PUBLICATIONS

Van Veen et al., "Beamforming: A Versatile Approach to Spatial Filtering", IEEE ASSP Magazine, Apr. 1, 1988, vol. 5, No. 2, pp. 4-24.

Wu et al., "Beacon-Aided Adaptive Localization of Noise Sources Aboard a Pass-By Railcar Using a Trackside Microphone Array", IEEE Transactions on Vehicular Technology, Oct. 2010, vol. 59, No. 8, pp. 3720-3727.

* cited by examiner

SELF-CALIBRATION OF MULTI-MICROPHONE NOISE REDUCTION SYSTEM FOR HEARING ASSISTANCE DEVICES USING AN AUXILIARY DEVICE

TECHNICAL FIELD

The present application relates to hearing assistance device comprising a noise reduction system and in particular to hearing assistance system for calibrating a noise reduction system of a hearing assistance device.

Embodiments of the disclosure may e.g. be useful in applications such as hearing assistance devices, e.g. hearing aids, headsets, ear phones, active ear protection systems, etc.

BACKGROUND

The following account of the prior art relates to one of the areas of application of the present application, hearing aids.

Noise reduction systems in hearing aids traditionally consist of two signal processing components:
i) a spatial noise reduction component (beamformer) which tries to emphasize signals originating from a specific direction, typically the front direction, assuming the hearing aid user "chooses with the nose", and
ii) a single-channel noise reduction system which often operates on the output of the directional noise reduction system, attempting to suppress the noise remaining in the signal.

The spatial noise reduction system often makes use of several fixed (=predetermined) beamformers. By using fixed beamformer building blocks in a time-varying manner, the actual beamformer system may still be time-varying/adaptive. The fixed beamformers are typically implemented by forming linear combinations of the input (microphone) signals. The problem to be solved in the present disclosure is essentially how to determine the coefficients of these linear combinations, i.e., the fixed beamformer weights, in a manner, which is optimized to the physical characteristics of the hearing aid user.

The fixed (or predetermined) beamformer weights may be determined off-line so that they realize certain prescribed spatial filtering characteristics. For example, in a minimum variance distortion-less response (MVDR) beamformer, it is desirable to implement a beam pattern, which has a gain of 0 dB in a certain direction, e.g., the frontal. In other cases, it is of interest to implement a target-cancelling beamformer, i.e., a beamformer which has a spatial null in the direction of the target, see e.g. [Kjems&Jensen; 2012] for an example.

Truly optimal beamformer weights are a function of several factors, including the physical characteristics of the user such as head shape and size, location and size of the pinnae, haircut, but also microphone locations, hearing aid shells, etc. In practice (so far), the fixed beamformer weights have been estimated, e.g. using a head-and-torso simulator (e.g. Head and Torso Simulator (HATS) 4128C from Brüel & Kjær Sound & Vibration Measurement A/S) by the hearing aid manufacturer and stored in a hearing aid memory. In this sense, the fixed beamformer weights are tailored to the HATS-model, i.e., exhibiting some sort of average human physical characteristics.

The problem is that fixed beamformers implemented like this are close-to-optimal for a HATS-model, but not for a specific hearing aid user. The present disclosure proposes a way for finding the optimal beamformer weights based on the physical appearance of the individual hearing aid user.

SUMMARY

An object of the present application is adapt a noise reduction system of a hearing assistance device to a particular user. A further object of embodiments of the application is to facilitate an adaptation to be made by the manufacturer, at a dispenser, or by a user him- or herself.

Objects of the application are achieved by the invention described in the accompanying claims and as described in the following.

A Hearing Assistance System:

In an aspect of the present application, an object of the application is achieved by a hearing assistance system comprising a hearing assistance device and an auxiliary device; the hearing assistance device comprising HD-a) a multitude M of input units $IU_i$, i=1, ..., M, adapted to provide or to receive a time-frequency representation $S_i(k,m)$ of a signal $s_i(n)$ at an $i^{th}$ input unit in a number of frequency bands and a number of time instances, k being a frequency band index, m being a time index, n representing time, and M being larger than or equal to two; and HD-b) a multi-input unit noise reduction system comprising a multi-channel beamformer filtering unit operationally coupled to said multitude of input units $IU_i$, i=1, ..., M, and configured to determine filter weights w(k,m) for providing a beamformed signal Y(k,m), wherein signal components from other directions than a direction of a target signal source are attenuated, whereas signal components from the direction of the target signal source are left un-attenuated or are attenuated less than signal components from said other directions;

the system comprising a user interface for activating a calibration mode in the auxiliary device and in the hearing assistance device;

the auxiliary device comprising

AD-a) an output transducer for converting an electric signal representative of a sound to an acoustic sound signal;

AD-b) a control unit for forwarding a calibration signal to the output transducer when said calibration mode is activated;

wherein the system is configured to estimate a look vector d(k,m) for a target signal originating from a target signal source located at a specific location relative to the user based on the electric calibration signal converted by the output transducer of the auxiliary device to an acoustic calibration sound signal, wherein said specific location relative to the user is the location of said output transducer of the auxiliary device.

An advantage of the present disclosure is that a calibration of the multi-microphone system is facilitated.

In an embodiment, calibration is made on a number of different 'typical' persons physical or artificial (e.g. models, dolls, e.g. a standard model, e.g. HATS), e.g. representing a typical child, a typical female, and a typical male person, and/or for a number of (typical) head sizes and/or forms and/or hair styles, and/or ear positions/sizes, and/or ages. Further, more variable parameters can be taken into account, such as position of the hearing assistance device(s) on the head, clothing, e.g. a scarf, a hat, etc. The resulting settings are then e.g. made available in a fitting software, for a dispenser (or user) to chose among and apply to the hearing assistance device in question. During calibration the hearing assistance device comprising the noise reduction system is mounted on the person in question (e.g. on such 'typical persons'). In an embodiment, the person is the 'end-user' of the hearing assistance device.

In the present context, the term 'beamforming' ('beamformer') is taken to mean to (provide) a 'spatial filtering' of a number of inputs sensor signals with the aim of attenuating signal components from certain angles relative to signal components from other angles in a resulting beamformed signal. 'Beamforming' is taken to include the formation of linear combinations of a number of sensor input signals (e.g. microphone signals), e.g. on a time-frequency unit basis, e.g. in a predefined or dynamic/adaptive procedure.

In an embodiment, the system is adapted to establish a communication link between the hearing assistance device and the auxiliary device to provide that information (e.g. control and status signals, e.g. related to the calibration procedure, possibly audio signals) can be exchanged or forwarded from one to the other.

The look vector $\underline{d}(k,m)$ is an M-dimensional vector comprising elements (i=1, 2, . . . , M), the $i^{th}$ element $d_i(k,m)$ defining an acoustic transfer function from the target signal source to the $i^{th}$ input unit (e.g. a microphone), or the relative acoustic transfer function from the $i^{th}$ input unit to a reference input unit. The vector element $d_i(k,m)$ is typically a complex number for a specific frequency (k) and time unit (m). The look vector $d(k,m)$ may be estimated from the inter input unit covariance matrix $\hat{R}_{ss}(k,m)$ based on the signals $s_i(k,m)$, i=1, 2, . . . , M measured at the respective input units when the calibration signal is played by the output transducer of the auxiliary device.

In an embodiment, the auxiliary device comprises the user interface for activating the calibration mode. In an embodiment, the user interface for activating a calibration mode is distributed between the hearing assistance device and the auxiliary device. In an embodiment, the calibration mode is activated in the hearing assistance device via an activation element in or on the hearing assistance device. In an embodiment, the calibration mode is activated in the auxiliary device via an activation element in or on the auxiliary device.

In an embodiment, the hearing assistance device and said auxiliary device are adapted to establish a wireless link between them. In an embodiment, the hearing assistance device comprises a wireless receiver for receiving data from the auxiliary device. In an embodiment, the auxiliary device comprises a wireless transmitter for transmitting data to the hearing assistance device. In an embodiment, audio processing system is configured to allow control signals for activating the calibration mode in the hearing assistance device to be transmitted from the auxiliary device to the hearing assistance device via the wireless link.

In an embodiment, the hearing assistance system is adapted to communicate one or more of the start time of the calibration signal, the chosen location of the auxiliary device relative to the user, and characteristics of the calibration signal to the hearing assistance device. Preferably, the calibration signal has a duration in time, a level and frequency content allowing an acoustic transfer function at relevant frequencies (apart from a scaling factor) from the auxiliary device to each of the input units to be determined. The acoustic transfer function between the output transducer of the auxiliary device and a given input unit of the hearing assistance device depends on the acoustic propagation path (including the distance and acoustic propagation properties of the user's head and body). In an embodiment, the calibration signal has a predefined duration in time, e.g. less than 2 s, e.g. ≤1 s. In an embodiment, the measurement of the propagated calibration signal is performed in the duration time. In an embodiment, the calibration signal comprises a broadband signal comprising all frequencies of interest, e.g. frequencies between a minimum and a maximum frequency, e.g. a sub-range in the range between 20 Hz and 8 kHz. In an embodiment, the calibration signal comprises a pulse or a train of pulses, e.g. a periodic train of pulses, e.g. with a repetition frequency ≥20 Hz. In an embodiment, the distance in time between successive pulses is larger than the reverberation time of the location where the calibration is performed (e.g. In an embodiment, the duration of the pulse is smaller than or equal to 2 ms, e.g. ≤1 ms. In an embodiment, the calibration signal comprises a white noise signal of a predefined duration, e.g. ≤1 s.

In an embodiment, the hearing assistance system is configured to determine filter weights for one or more fixed beamformers based on said estimate of a look vector $\underline{d}(k,m)$. In an embodiment, a number of pre-determined sets of look vectors $d_{pd}$, each set encompassing look vectors estimated for different directions (θ, φ), and ranges (|r|), e.g. for different persons U are stored in a memory of the hearing assistance device(s). In an embodiment, a look vector for a location (θ, φ, |r|)$_x$ (defined by vector $r_{xsrc}$ from the user, cf. FIG. 3A) of a target sound source different from the calibrated (front) direction is estimated by comparing the calibrated front look vector $d_{cal}$ determined for distance $r_{cal}$ (θ=θ$_{front}$, φ=φ$_{front}$) with corresponding front look vectors stored in memory ($d_{pd}$(θ=θ$_{front}$, φ=φ$_{front}$, |r|=r$_{cal}$, person). If/when a close match is found for a front look vector for a given person-type, the look vector corresponding to (θ, φ, |r|)$_x$ of the relevant vector $r_{xsrc}$ as stored in the memory for the given person-type is selected and used as an estimate of the true look vector in the current situation.

In an embodiment, the hearing assistance system is configured to determine filter weights for one or more fixed beamformers based an assumption of the spatial noise distribution. In an embodiment, the distribution of the noise is assumed to be spatially isotropic (e.g. spherically or cylindrically isotropic). In an embodiment, the distribution of the noise is assumed to originate exclusively from a predefined angle segment relative to (e.g. to the rear of) the user.

In an embodiment, the fixed beamformers comprise:
an enhanced omni beamformer for providing a beamformed signal $E_{omni}(k,m)$ with a gain of 0 dB when a signal is received from the target direction/location, and/or
a target cancelling beamformer for providing a target-cancelling beamformed signal $C_R(k,m)$, which ideally rejects a signal played from the target direction/location. Other fixed beamformers could be relevant, e.g. a front hyper-cardioid beamformer for (maximally, assuming spatially isotropic noise) enhancing a signal received from the target direction/location—relative to signals from other directions—more than the enhanced omni beamformer. Alternatively, a fixed beamformer for maximum suppression of signals from a rear-plane relative to the user could be of use, etc.

In an embodiment, the hearing assistance device further comprises a single channel post-processing filter unit operationally coupled to said multi-channel beamformer filtering unit and configured to provide an enhanced signal $\hat{S}(k,m)$. In an embodiment, the multi-channel variable beamformer filtering unit comprises an MVDR filter providing filter weights $w_{mvdr}(k,m)$, said filter weights $w_{mvdr}(k,m)$ being based on a look vector $d(k,m)$ and an inter-input unit covariance matrix $R_{vv}(k,m)$ for the noise signal. MVDR is an abbreviation of Minimum Variance Distortion-less Response, Distortion-less indicating that the target direction is left unaffected; Minimum Variance: indicating that signals from any other direction than the target direction is maximally suppressed).

An aim of the single channel post filtering process is to suppress noise components from the target direction (which has not been suppressed by the spatial filtering process (e.g. an MVDR beamforming process). It is a further aim to suppress noise components during when the target signal is present or dominant as well as when the target signal is absent. In an embodiment, the single channel post filtering process is based on an estimate of a target signal to noise ratio for each time-frequency tile (m,k). In an embodiment, the estimate of the target signal to noise ratio for each time-frequency tile (m,k) is determined from the beamformed signal and the target-cancelled signal.

In an embodiment, the hearing assistance system comprises a control unit configured to compare beamformer weights $w_{cal}(k,m)$ resulting from the calibration to a set of default beamformer weights $w_{pd}(k,m)$ and to provide a difference measure.

In an embodiment, the hearing assistance system is adapted to provide that default beamformer weights are used, if the difference measure is above a predefined threshold. In an embodiment, the default beamformer weights $w_{pd}(k,m)$ (stored in a memory of the hearing assistance device(s)) are used, if the difference measure indicative of a difference between two sets of filter weights is above a predefined threshold (e.g. defined by a statistical distance measure). In an embodiment, the hearing assistance system comprises a noise estimation unit for estimating a current background noise in the calibration mode of operation of the system (in particular during the calibration of the beamformer, i.e. when the calibration signal is played by the auxiliary device). In an embodiment, the default beamformer weights are used, if the ambient noise is above a predefined threshold level.

In an embodiment, the hearing assistance system is configured to provide that the calibration signal is adapted to the current noise level and/or spectrum, by shaping the calibration signal to ensure a predetermined (minimum) calibration signal to noise ratio (at least over a predefined frequency range, such as all frequencies) and/or the duration in time of the calibration signal. In an embodiment, the level and/or spectrum of the background noise is monitored, e.g. by the auxiliary device, e.g. as a first action of the calibration procedure (before the calibration signal is formed and played via the output transducer of the auxiliary device). In an embodiment, the resulting look vector determined based on the received calibration signal is accepted and stored in a memory of the hearing assistance device, if said level and/or spectrum of the current background noise is within acceptable limits. In an embodiment, the calibration sound is shaped (e.g. in level, frequency, and/or temporal characteristics, e.g. duration) to take account of the current background noise (e.g. to provide a certain minimum (calibration) signal to noise ratio at all or at relevant frequencies), and to estimate the covariance matrix $R_{ss}$ right after each impulse to reduce impact of reverberation, cf. FIG. 4. Alternatively, the measurement is discarded (no look vector is stored), if the noise level is above a predetermined threshold value (e.g. at predetermined frequencies).

In an embodiment, the fixed beamformer(s) is/are determined from the estimated look vector $\widehat{d(k,m)}$ and an estimate of the inter-input unit covariance matrix $\hat{R}_{vv}(k,m)$ of the noise $v_i$ impinging on the respective input units (i=1, 2, ..., M). [Kjems&Jensen; 2012] describe various aspects of noise covariance matrix estimation in a multi-microphone speech configuration.

In an embodiment, an estimate of the noise covariance matrix, termed $\hat{R}_{vv,diffuse}(k,m)$, is predetermined and stored in a memory of the hearing assistance device. The noise covariance matrix reflects the known (or assumed) information regarding the spatial distribution of the noise (spatial fingerprint of the noise). $\hat{R}_{vv,diffuse}(k,m)$ is one such noise covariance matrix assuming a diffuse (spatially isotropic) noise. Other noise covariance matrices may be used as the case may be, e.g. $\hat{R}_{vv,rear}(k,m)$ assuming noise only from the rear of the user.

In an embodiment (where the target signal component and the noise signal component are un-correlated), the inter-input unit covariance matrix $R_{ss}$ of the noisy signal s is a sum of the inter-input unit covariance matrix $R_{xx}$ of the target signal x and the inter-input unit covariance matrix $R_{vv}$ of the noise signal.

In an embodiment, at least one of the M input units comprises a microphone. In an embodiment, a majority, such as all, of the M input units comprises a microphone. In an embodiment, M is equal to two. In an embodiment, M is larger than or equal to three. In an embodiment, a first one of the M input units is located in an audio processing device (e.g. a hearing assistance device). In an embodiment, at least one of the other M input units is located a distance to the first input unit that is larger than a maximum outer dimension of the audio processing device where the first input unit is located. In an embodiment, a first of the M input unit is located in a first audio processing device and a second of the M input units is located in another device, the audio processing device and the other device being configured to establish a communication link between them.

In an embodiment, the inter-input unit covariance matrices are estimated by a maximum likelihood based method (cf. e.g. [Kjems&Jensen; 2012]). In an embodiment, the audio processing system is configured to make maximum likelihood estimates of the inter input unit covariance matrix $\hat{R}_{ss}(k,m)$ of the noisy signal based on a number D of observations.

In an embodiment, the hearing assistance system comprises a voice activity detector for estimating whether or not a target signal is present or dominating at a given point in time. In an embodiment, the method comprises estimating whether or not a target signal is present or dominating at a given point in time, e.g. using a voice activity detector. In an embodiment, the spatial fingerprint of the noise signal, e.g. noise covariance matrices, is updated when it is estimated that the target signal is absent. In an embodiment, the spatial fingerprint of the target signal, e.g. look vectors, is updated when it is estimated that the target signal is present or dominant. In an embodiment, the method comprises estimating whether or not a voice (e.g. speech) is present or dominating at a given point in time.

In an embodiment, the auxiliary device comprises an audio gateway device, a mobile telephone, or a computer. In an embodiment, the auxiliary device comprises or forms part of a fitting system. In an embodiment, the auxiliary device comprises a portable communication device, e.g. a SmartPhone or a tablet computer. In an embodiment, the auxiliary device comprises a remote control device for the hearing assistance device.

In an embodiment, the hearing assistance system comprises a sensor for allowing a user a) to locate the auxiliary device at a predetermined angle and/or height and/or distance relative to the user and/or b) to track the location of the auxiliary device relative to the user. Deciding on the correct location of the external device may be done manually by the user or automatically by the device, e.g. using gyroscopes, accelerometers, a camera with visual feedback from the user (e.g. eye tracking), etc., in the device.

In an embodiment, the hearing assistance system is adapted to provide a frequency dependent gain to compensate for a hearing loss of a user. In an embodiment, the hearing assistance device comprises a signal processing unit for enhancing the input signals and providing a processed output signal.

In an embodiment, the hearing assistance device comprises an output transducer for converting an electric signal to a stimulus perceived by the user as an acoustic signal. In an embodiment, the output transducer comprises a number of electrodes of a cochlear implant or a vibrator of a bone conducting hearing device. In an embodiment, the output transducer comprises a receiver (speaker) for providing the stimulus as an acoustic signal to the user.

In an embodiment, the hearing assistance device are portable device, e.g. a device comprising a local energy source, e.g. a battery, e.g. a rechargeable battery.

In an embodiment, the hearing assistance device comprises a forward or signal path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain according to a user's particular needs. In an embodiment, the left and right hearing assistance device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing assistance device comprises an analogue-to-digital (AD) converter to digitize an analogue input with a predefined sampling rate, e.g. 20 kHz. In an embodiment, the hearing assistance devices comprise a digital-to-analogue (DA) converter to convert a digital signal to an analogue output signal, e.g. for being presented to a user via an output transducer.

In an embodiment, the hearing assistance device, e.g. the input unit, e.g. a microphone unit, and or a transceiver unit, comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing assistance device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing assistance device is split into a number NI of frequency bands, where NI is e.g. larger than 5, such as larger than 10, such as larger than 50, such as larger than 100, such as larger than 500, at least some of which are processed individually.

In an embodiment, the hearing assistance device comprises a level detector (LD) for determining the level of an input signal (e.g. on a band level and/or of the full (wide band) signal). The input level of the electric microphone signal picked up from the user's acoustic environment is e.g. a classifier of the environment. In an embodiment, the level detector is adapted to classify a current acoustic environment of the user according to a number of different (e.g. average) signal levels, e.g. as a HIGH-LEVEL or LOW-LEVEL environment.

In an embodiment, the hearing assistance device comprises an acoustic (and/or mechanical) feedback detection and/or suppression system. In an embodiment, the hearing assistance device further comprises other relevant functionality for the application in question, e.g. compression, etc.

In an embodiment, the hearing assistance device comprises a listening device, e.g. a hearing aid, e.g. a hearing instrument, e.g. a hearing instrument adapted for being located at the ear or fully or partially in the ear canal of a user, or for being fully or partially implanted in the head of a user, a headset, an earphone, an ear protection device or a combination thereof.

Use:

In an aspect, use of a hearing assistance device as described above, in the 'detailed description of embodiments' and in the claims, is moreover provided. In an embodiment, use in a binaural hearing aid system is provided.

A Method:

In an aspect, a method of calibrating a multi-input unit noise reduction system of a hearing assistance device, the method comprising a) Providing a hearing assistance device comprising the multi-input unit noise reduction system and a multitude M of input units, where M is larger than or equal to two;

b) Providing an auxiliary device comprising an output transducer;

c) Locating the auxiliary device within a predetermined distance of a user wearing said hearing assistance device, thereby defining a specific location of (the output transducer of) the auxiliary device relative to (the hearing assistance device of) the user;

d) Initiating a calibration mode in the hearing assistance device and the auxiliary device;

e) Providing an acoustic calibration signal by the output transducer of the auxiliary device;

f) Providing a time-frequency representation Si(k,m) of the calibration signal si(n) at an ith input unit, i=1, 2, . . . , M, in a number of frequency bands and a number of time instances, k being a frequency band index and m being a time index is furthermore provided by the present application, the method further comprising g) estimating a look vector d(k,m) for a target signal originating from a target signal source located in said specific location relative to the user based on said time-frequency representation Si(k,m) of the calibration signal si(n), i=1, 2, . . . , M; and h) determining optimal beam former weights based on said estimated look vector d(k,m).

It is intended that some or all of the structural features of the system described above, in the 'detailed description of embodiments' or in the claims can be combined with embodiments of the method, when appropriately substituted by a corresponding process and vice versa. Embodiments of the method have the same advantages as the corresponding systems.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, and used when read directly from such tangible media, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

DEFINITIONS

In the present context, a 'hearing assistance device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing assistance device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing assistance device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

More generally, a hearing assistance device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing assistance devices, an amplifier may constitute the signal processing circuit. In some hearing assistance devices, the output means may comprise an output transducer, such as e.g. a loudspeaker for providing an air-borne acoustic signal or a vibrator for providing a structure-borne or liquid-borne acoustic signal. In some hearing assistance devices, the output means may comprise one or more output electrodes for providing electric signals.

In some hearing assistance devices, the vibrator may be adapted to provide a structure-borne acoustic signal transcutaneously or percutaneously to the skull bone. In some hearing assistance devices, the vibrator may be implanted in the middle ear and/or in the inner ear. In some hearing assistance devices, the vibrator may be adapted to provide a structure-borne acoustic signal to a middle-ear bone and/or to the cochlea. In some hearing assistance devices, the vibrator may be adapted to provide a liquid-borne acoustic signal to the cochlear liquid, e.g. through the oval window. In some hearing assistance devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing assistance system' refers to a system comprising one or two hearing assistance devices, and a 'binaural hearing assistance system' refers to a system comprising two hearing assistance devices and being adapted to cooperatively provide audible signals to both of the user's ears. Hearing assistance systems or binaural hearing assistance systems may further comprise 'auxiliary devices', which communicate with the hearing assistance devices and affect and/or benefit from the function of the hearing assistance devices. Auxiliary devices may be e.g. remote controls, audio gateway devices, mobile phones, public-address systems, car audio systems or music players. Hearing assistance devices, hearing assistance systems or binaural hearing assistance systems may e.g. be used for compensating for a hearing-impaired person's loss of hearing capability, augmenting or protecting a normal-hearing person's hearing capability and/or conveying electronic audio signals to a person.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1:
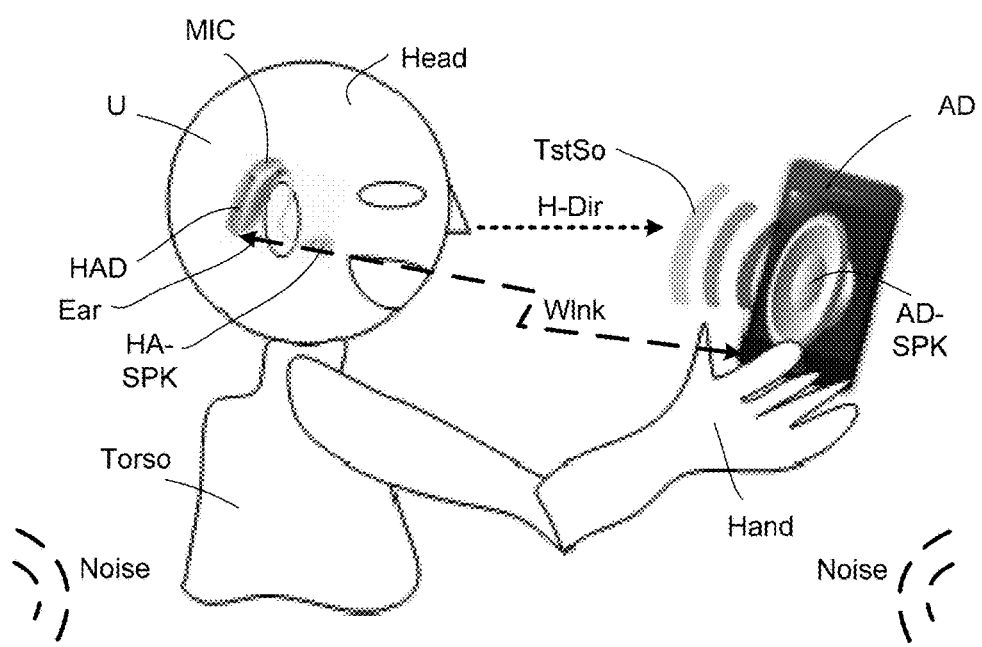
FIG. 1 schematically shows a situation of performing a self calibration routine of hearing assistance device noise reduction system using an external device as proposed in the present disclosure, FIG. 2 schematically illustrates respective block diagrams of embodiment of a multi-microphone noise reduction system according to the present disclosure, FIG. 2A showing an embodiment comprising a beamformer filter and a single-channel post-processing filter for noise reduction, FIG. 2B showing an embodiment additionally comprising a target-cancelling beamformer filter, FIG. 3 schematically illustrates a scenario for estimating beamformers for different locations than that of a calibration source, FIG. 3A showing an intended location of a target sound source and a location of the sound source during calibration of the beamformer look vector, and FIG. 3B showing an example of predetermined locations of sound sources relative to a user for which look vectors have been estimated and stored in a memory of the hearing assistance device in advance of its use, FIG. 4 schematically illustrates a number of acoustic paths between a sound source and a receiver of sound located in a room (FIG. 4A), an exemplary illustration of amplitude versus time for a sound signal in the room (FIG. 4B), and a measurement procedure for calibrating a noise reduction system according to the present disclosure (FIG. 4C), FIG. 5 schematically illustrates a conversion of a signal in the time domain to the time-frequency domain, FIG. 5A illustrating a time dependent sound signal (amplitude versus time) and its sampling in an analogue to digital converter, FIG. 5B illustrating a resulting 'map' of time-frequency units after a (short-time) Fourier transformation of the sampled signal.

FIG. 1 shows a scenario allowing a user (U) of a hearing assistance device (HAD) to perform a self-calibration of beamformer weights of a noise reduction system, using an external (auxiliary) device (AD) comprising a loudspeaker (SPK). The auxiliary device (AD) and the hearing assistance device(s) (HAD) are configured to allow the establishment of a wireless link between them (e.g. to inform the hearing assistance device about the initiation of a calibration procedure). In an embodiment, the external (auxiliary) device (AD) comprises or is constituted by a mobile phone. Alternatively, it may form part of a fitting system. The aim of the activity is to calibrate the noise reduction system in the (or each) hearing assistance device (HAD) by playing a calibration sound (TstSo) from the external device (AD) that is captured by the input units (MIC) of the hearing assistance device or each of the hearing assistance devices in case the user (U) wears a binaural hearing assistance device system. Further, additional microphones (whose signals are transmitted to corresponding input units of the hearing assistance device) may be located in other devices than the hearing assistance device itself (e.g. in a communication device worn by the user (e.g. an audio gateway or a cellular telephone), in a wireless microphone, or the like).

An example of such calibration procedure is as follows:
A) The external device (AD) is held in front of the user (U, e.g. in a stretched arm (Hand)).
B) When the external device (AD, e.g. its speaker, AD-SPK) is in the horizontal plane or direction (H-Dir) of the hearing assistance device users ears (or eyes) (Ear), and in the frontal position, the calibration procedure is initiated (e.g. by an activation of a calibration mode in the external device, e.g. an APP of a SmartPhone). It is generally assumed that the ambient noise (cf. Noise in FIG. 1, e.g. in the form of additive or convolutional noise) during the calibration measurement is much smaller than the calibration signal, i.e. that there is essentially no noise present. In practice, this may be hard to achieve, and one or more precautions taking account for such situations are preferably included in the procedure (thereby increasing its robustness). In an embodiment, the routine may be terminated, if the background noise (Noise) level or reverberation level, e.g. as measured by the external device or the hearing assistance devices, is too high. The ambient noise may be monitored in various ways (e.g. as described in US2011026725A1, teaching the monitoring of the energy of the first-difference of filter coefficients of an adaptive filter for estimating a feedback path over time and applying a predefined threshold criterion to the change in energy content from one time instance to another to determine an acceptable impact of the ambient noise). In an embodiment, the calibration signal is adapted to the current noise level and spectrum, by shaping the calibration signal to ensure a predetermined (minimum) calibration signal to ambient noise ratio (at least over a predefined frequency range, such as at all frequencies). Deciding on the correct location of the external device may be done manually by the user or automatically by the device, e.g. using gyroscopes, accelerometers, a camera with eye tracking, etc., in the device.
C) The auxiliary device (AD) informs the hearing assistance device(s) (HAD) via wireless communication link (Wink) that the calibration routine is about to be initiated (setting the hearing assistance device(s) in a calibration mode) and emits a calibration sound (TstSo), e.g. a click, a click train, or a broadband noise signal, from the loudspeaker (AD-SPK).
D) As further detailed below, the resulting signal picked up by the hearing assistance devices' microphones (MIC) can be used to determine the optimal fixed beamformer weights, e.g., the optimal delay-and-sum beamformer with unity gain in the frontal direction, a target-cancelling beamformer with a spatial null exactly in the frontal direction, etc. (cf. e.g. FIG. 2).

An advantage of the in-situ determined beamformer weights is that they implement an individualized beamformer, which is optimal for the hearing assistance device user (U) in question. Specifically, this procedure results in fixed beamformers designed to take into account the physical characteristics of the user (U), e.g. the head (Head), the ears (Ear), the body (Torso), the hair style, etc. Such characteristics of a user may further change across time, in particular for children, but also for adults (e.g. hair cuts, etc.). The exact location of the hearing assistance device(s) may differ slightly from day to day. The microphones of the hearing assistance device(s) may not have exactly the same characteristics as the microphones used by the hearing assistance device manufacturer, when determining the default hard-wired beamformer weights, such characteristics may further drift across time, etc.

The calibration routine may preferably be equipped with a safety procedure: The beamformer weights resulting from the calibration routine may be compared to a set of default beamformer weights. If for example the two sets of weights are very different, the calibration routine may be declared invalid, and the default weights are used. The same may be the case, if the ambient noise is above a predefined threshold level.

1. Example of Noise Reduction System

Figure 2A:
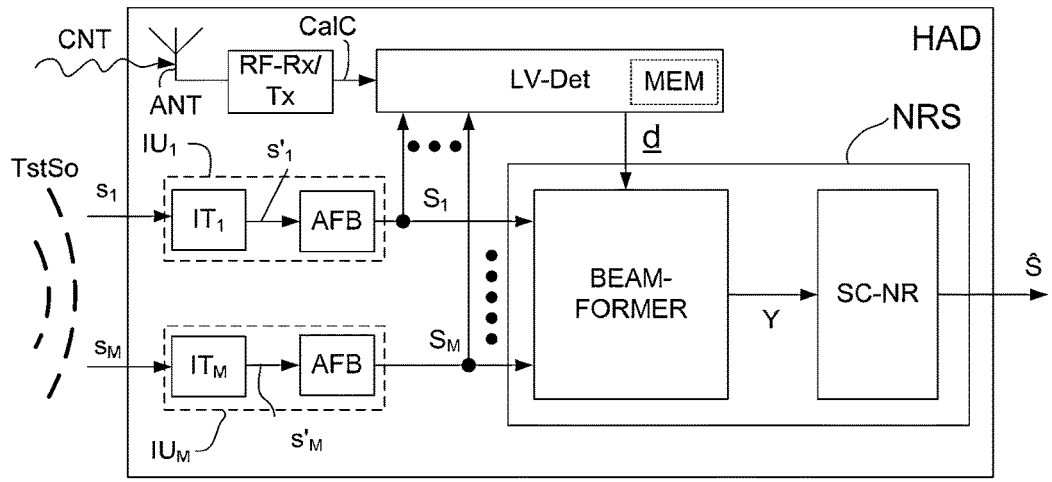
Figure 2B:
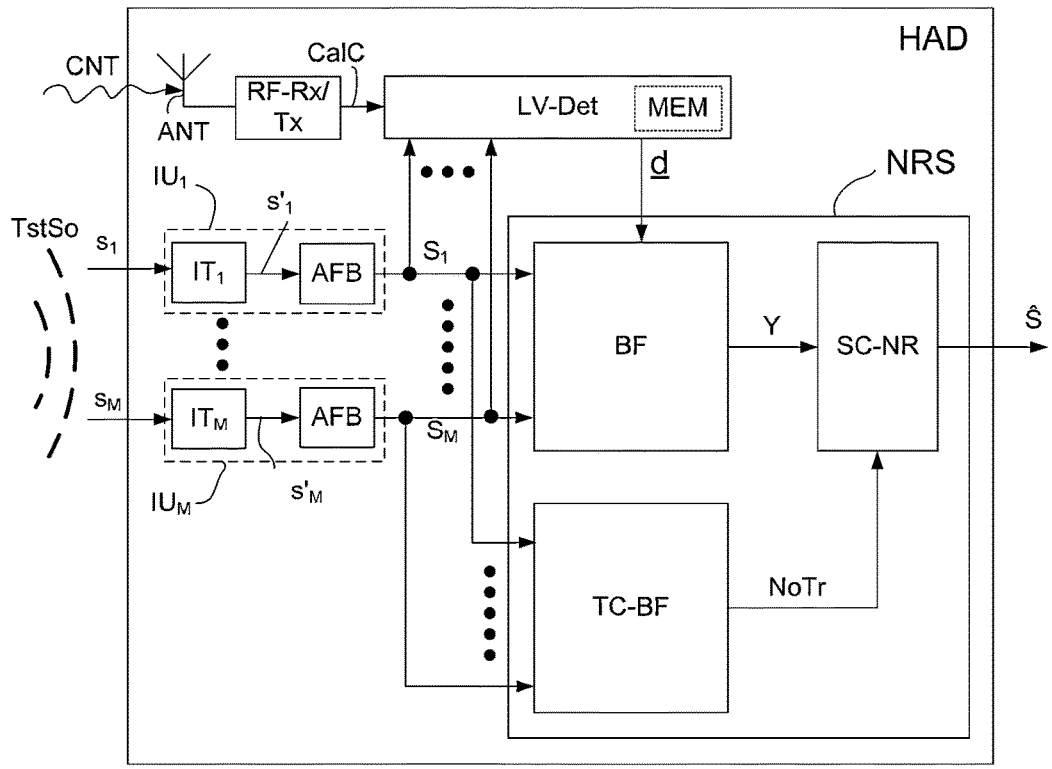

FIG. 2A and FIG. 2b show exemplary block diagrams of respective embodiments of a hearing assistance device (HAD) comprising a multi input unit (e.g. a multi-microphone) noise reduction system (NRS) (here shown with M input units, e.g. microphone units). The multi input unit noise reduction system (NRS) comprises a multi input beamformer filter unit (BF in FIGS. 2A and 2B, e.g. a minimum variance distortion-less response (MVDR) beamformer) followed by a single-channel noise reduction system (SC-NR in FIGS. 2A and 2B). The beamformer (BF) provides a beamformed signal Y with a gain of 0 dB, when a signal is received from the target direction/location. The embodiment of FIG. 2B further comprises a target-cancelling beamformer filter unit (TC-BF) providing a target-cancelling beamformed signal, which ideally rejects (in practice attenuates maximally) a signal played from the target direction/location. The target-cancelling beamformer filter unit potentially comprises several (up to M−1) target cancelling beamformers. The target-cancelling beamformer filter unit (TC-BF) provides control signal NoTr indicative of the noise present in the beamformed signal Y and configured to control the single channel post-filtering unit (SC-NR). The signals depend on time and frequency indices (m,k), cf. analysis filter bank units (AFB) in each input unit $IU_i$, connected to each input elements ($IT_i$), e.g. an input transducer such as a microphone. Input sound signals $s_1(n), \ldots, s_M(n)$ received at respective input unit $IU_1, \ldots, IU_M$ are thus provided in a time-frequency representation as signals $S_1(k,m), \ldots, S_M(k,m)$. In the embodiments of FIGS. 2A and 2B, independent beamforming and single-channel post-filter operations are carried out for each frequency band (k). The output Ŝ of the noise reduction system (NRS), which is a noise reduced version of the microphone signals ($S_1, \ldots, S_M$), is e.g. subsequently amplified (and compressed), preferably according to a user's particular needs, e.g. to compensate for the user's hearing impairment) and presented for the hearing assistance device user (U) via the loudspeaker (cf. HA-SPK in FIG. 1).

The hearing assistance device further comprises antenna and transceiver circuitry (ANT, RF-Rx/Tx) for establishing a wireless communication link to the auxiliary device (AD) in FIG. 1), e.g. for receiving a calibration control signal CNT from the auxiliary device. The idea is that the calibration control signal (CalC) fed from the transceiver circuitry (RF-Rx/Tx) to the look vector determination unit (LV-Det) comprises a 'start calibration procedure' indication from the auxiliary (calibration) device (AD). The auxiliary device contains the calibration sound source (speaker), e.g. forming part of a dedicated calibration system (e.g. a fitting system) or a portable communication device, e.g. a SmartPhone or the like. When the auxiliary device sends the CNT (CalC) signal (e.g. at the request of a user), the auxiliary device subsequently emits the calibration sound TsTSo. When the hearing assistance device (HAD) receives the 'START of calibration' indication, it prepares for the measurement of the received calibration sound (e.g. to monitor and evaluate the background noise and to measure the received response signals caused by the calibration sound TsTSo a predefined time after the reception of the 'start calibration procedure' signal). Based on the evaluation of the background noise, measurement may be stopped (if the background noise level is too high), or the calibration signal may be modified in magnitude at different frequencies (shaped) and/or the duration of the measurement period may be adapted (e.g. increased with increasing ambient noise level). The look vector determination unit (LV-Det) determines a current look-vector based on the microphone signals ($S_1, \ldots, S_M$) representing the calibration-signal TstSo. The unit LV-Det determines the look vector (comprising transfer functions from the calibration sound source to each of the input units (e.g. microphones) or scaled versions thereof) for the direction to (and distance to) the auxiliary device relative to each of the input units of the user's hearing assistance device(s) (HAD). Preferably, the look vector is stored in a memory (MEM) of the hearing assistance device. The resulting look vector $\underline{d}$ is fed to the beamformer (if the result of the background noise measurement is acceptable). The determination of the look vector is e.g. based on an inter-microphone covariance matrix, $$\hat{R}_{ss}(k) = \frac{1}{N} \sum_m s(m,k) s^H(m,k)$$

where s(m,k) is a vector $s(m,k)=[S_1(m,k), \ldots, S_M(m,k)]^T$ defining the calibration signal as received by the input units of the hearing assistance device.

The multi input unit noise reduction system (NRS) may comprise a beamformer (BF) with a predetermined (e.g. periodically fixed, e.g. after a calibration) spatial target fingerprint (e.g. look vector) and a fixed spatial noise fingerprint (e.g. noise covariance matrix), cf. FIG. 2A. It may alternatively comprise a beamformer (BF) with a predetermined spatial target fingerprint and a variable spatial noise fingerprint (e.g. target-cancelling beamformer TC-BF, FIG. 2B). Finally, the multi input unit noise reduction system (NRS) may comprise adaptive beamformers for implementing variable spatial target and noise fingerprints.

1A. Calibration of Beamformers:

The following relates to the block BF in FIG. 2. For each frequency index k, the NRS system makes use of the output of pre-determined (calibrated) beamformers, which can be formulated in terms of two quantities (which are frequency dependent): A look vector $d(k) \in \mathbb{C}^M$ and a noise covariance matrix $R_{vv}(k) \in C^{M \times M}$, where $C^M$ is the set of M-dimensional complex vectors, and $C^{M \times M}$ is the set of M×M-dimensional complex matrices. The proposed self-calibration routine is a method for estimating the look vector d(k). In an embodiment, the noise covariance matrix, whose estimate is called $\hat{R}_{vv,diffuse}(k)$ (assuming isotropic noise) is predetermined and stored in a memory of the hearing assistance device device (cf. e.g. MEM of FIG. 2).

1B. Calibration of Fixed Look Vector d(m,k):

During self-calibration, the look vector d(k) is estimated as follows. When the calibration sound (TstSo in FIG. 1) is emitted by the external device (AD-SPK of AD in FIG. 1), the resulting inter-microphone covariance matrix $R_{ss}(k)$ for microphones $Mic_1$, $Mic_2$ is estimated for each frequency k:

$$\hat{R}_{ss}(k) = \frac{1}{N} \sum_m s(m,k) s^H(m,k),$$

where $s(m,k) = [s(m,k,1) s(m,k,2)]^T$ and s(m,k,i) is the output of the analysis filter bank for microphone i, at time frame m and frequency index k, and N is the number of time frames considered in the estimation. For a true point source, the signal impinging on the array would be of the form s(m,k)=s(m,k)d(k) such that (assuming that signal s(m,k) is stationary) the theoretical target covariance matrix $R_{ss}(k)=E[s(m,k)s^H(m,k)]$ would be of the form $$R_{ss}(k) = \phi_{ss}(k) d(k) d^H(k),$$

i.e., the eigenvector of $R_{ss}(k)$ corresponding to the non-zero eigenvalue is proportional to d(k). Hence, our look vector estimate $\hat{d}(k)$ is defined as the eigen vector corresponding to the largest eigen value of the estimated target covariance matrix $\hat{R}_{ss}(k)$. Preferably, the look vector is normalized to unit length, that is:

$$d(k) := \frac{d(k)}{d^H(k) d(k)},$$

such that $||d||^2 = 1$. The look vector estimate d(k) thus encodes the physical direction and distance of the target source, it is therefore also called the look direction. Alternatively, the look vector may be normalized to have a '1' at the position of the reference input unit (e.g. a reference microphone).

1C. Computing the Fixed Beamformers

In the embodiment of FIGS. 2A and 2B, predetermined (calibrated) beamformers may be found in terms of the estimated look vector $\hat{d}(k)$ and the noise covariance matrix $\hat{R}_{vv,diffuse}(k)$ as follows (wherein it is assumed that the look vector as well as the noise covariance matrix are predetermined).

An enhanced omni beamformer (FIG. 2A) is given by $$w_{EO}(k) = \hat{d}(k) \hat{d}^*(k, i_{ref}),$$

where $i_{ref}$ is the index of the reference microphone. It can be shown that this beamformer is in fact the minimum variance distortionless response (MVDR) beamformer for the case where the noise covariance matrix is a scaled identity (this would occur when the microphone signals are dominated by microphone noise, i.e., e.g. at low input levels).

The target-cancelling beamformer (TC-BF in FIG. 2B) is given by the first column of the matrix $I - d(k) d^H(k)$, where I is the M×M (e.g. 2×2) identity matrix, that is (for M=2)

$$W_R(k) = \begin{bmatrix} 1 \\ 0 \end{bmatrix} - \hat{d}(k) \hat{d}^*(k,1).$$

Where '1' refers to microphone #1 as the reference microphone. In such case, it is the goal of the noise reduction system (NRS) to estimate speech as observed by microphone#1. It is easy to verify that for a noisy input signal of the form $Y(k) = s(k) \hat{d}(k) + V(k)$, i.e., the input consists of a point target source S and additive noise, the output of $W_R(k)$ is not related to the target signal $s(k) \hat{d}(k)$, but only to the noise component V(k). In other words, $W_R(k)$ is a target-cancelling beamformer.

A front hyper-cardioid beamformer (FIG. 2A, alternative to enhanced omni) is, in fact, the MVDR beamformer for the situation where the noise field is diffuse (that is, homogenous and spherically isotropic). We approximate this noise condition with a situation where the noise is cylindrically isotropic. In this case, the MVDR beamformer weight vector $W_H$, is given by $$W_H(k) = \frac{\hat{R}_{vv,diffuse}^{-1}(k) \hat{d}(k) \hat{d}^*(k, i_{ref})}{\hat{d}^H(k) \hat{R}_{vv,diffuse}^{-1}(k) \hat{d}(k)},$$

where $\hat{R}_{vv}(k)$ is the inter-microphone noise covariance matrix for the diffuse noise situation (predetermined). It can be shown that this beamformer minimizes the noise power in its output under the constraint that the target component is unchanged.

In summary, the self-calibration procedure may e.g. result in the determination filter coefficients of three optimal, individualized (calibrated) beamformers:

$w_{EO}(k)$: filter coefficients for enhanced omni beamformer $W_R(k)$: filter coefficient for rear-beamformer (target cancelling beamformer)

$W_H(k)$: filter coefficients for hyper-cardioid beamformer (frontal beamformer).

In the description above, the fixed beamformers $w_{EO}(k)$, $W_R(k)$, $W_H(k)$ are determined based on estimate $\hat{R}_{ss}(k)$ of the target signal covariance matrix, and estimates $\hat{R}_{vv}(k)$ of the inter-microphone covariance of the noise field. Instead of estimating these quantities via batch estimation as used above, they may be updated recursively.

2. Application Examples:

2A. Estimating Beamformers for Different Locations than the Calibration Source

The idea described above is to estimate beamformers "pointing" at the location of the calibration signal. For example, the enhanced omni beamformer $w_{EO}(k)$ has unit gain for signals originating from the location of the calibration source, and the target-cancelling beamformer $W_R(k)$ completely eliminates signals from this direction. In some cases, it might be desirable to determine the weights of beamformers "pointing" towards other locations than that of the calibration signal. To be specific, consider the case where the calibration signal originates from the frontal direction (0 degrees) and a range of 1 m (cf. $r_{cal}$ in FIG. 3A), but we are interested in determining the weights of beamformers pointing towards 30 degrees, 2 m (cf. $r_{xsrc}$ in FIG. 3A). This could e.g. be accomplished by storing in memory a number of pre-determined sets of look vectors d, each set encompassing look vectors estimated for different (direction ($\phi$), range (|r|)) pairs for different persons U (($\phi_j$, $r_{sq}$, $U_p$), i=1, 2, ..., $N_\phi$, q=1, 2, ..., $N_r$, and u=1, 2, ..., $N_U$). FIG. 3B shows a number of predefined orientations of the look vector relative to a user. FIG. 3B illustrates predefined locations of a target source $S_q$ relative a user (U) defined by vectors $r_{sq,p}$, (q=1, 2, ..., 8, p=a, b), or angle $\phi_j$ (j=1, 2, ..., 8) and distance $r_{sq,p} = |r_{sq,p}|$ (p=a, b). In FIG. 3B, it is assumed that the sound source $S_s$ is located in the same plane as the microphones of the left and right hearing assistance devices (HAD$_l$ and HAD$_r$). In an embodiment, predefined look vectors (and/or filter weights) for the respective multi-channel beamformer filtering units of the multi-input unit noise reduction systems of the left and right hearing assistance devices are determined in advance and stored in a memory of the left and right hearing assistance devices (cf. e.g. MEM in FIG. 2). Predefined angles $\phi_j$, j=1, 2, ..., 8 distributed in the front half plane (with respect to the user's face) corresponding to x≥0 and in the rear half plane corresponding to x<0 are exemplified in FIG. 3B. In this example, the density of predefined angles is larger in the front half plane than in the rear half plane. In the example of FIG. 3B, $\phi_1$-$\phi_7$ are located in the front half plane (e.g. evenly with 30° between them from $\phi_1$=−90° to $\phi_7$=+90°), whereas $\phi_8$ is located in the rear half plane ($\phi_8$=180°). For each predefined angle $\phi_j$, a number of distances $r_{sq,p}$ may be defined, in FIG. 5 two different distances, denoted a and b ($r_{sqb}$~2*$r_{sqa}$), are indicated. Any number of predefined angles and distances may be defined in advance and corresponding look vectors and/or filter weights determined and stored in a memory of the respective left and right hearing assistance devices (or be accessible from a common database of the binaural hearing assistance system, e.g. located in an auxiliary device, e.g. a SmartPhone). In an embodiment, the user interface is implemented as an APP of a SmartPhone. The predefined look vectors (or beamformer weights) may e.g. be determined prior to normal operation of the hearing aid device by measurement for different directions and distances on a model user, e.g. a Head and Torso Simulator (HATS) 4128C from Brüel & Kjær Sound & Vibration Measurement A/S 'equipped' with first and second hearing assistance devices. Different physical or model users may be used to determine look vectors for different persons (e.g. different size heads, different hair styles, etc.). The predetermined look vectors may preferably be stored in a memory of the hearing assistance device(s), e.g. prior to its fitting to a particular user (e.g. during manufacturing).

Figure 3A:
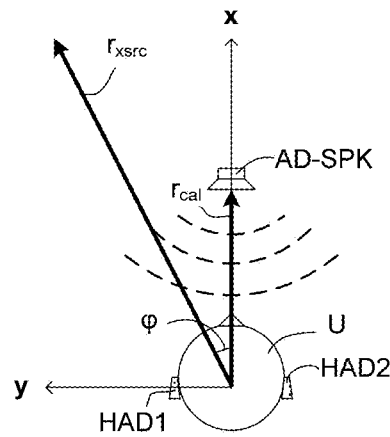
Figure 3B:
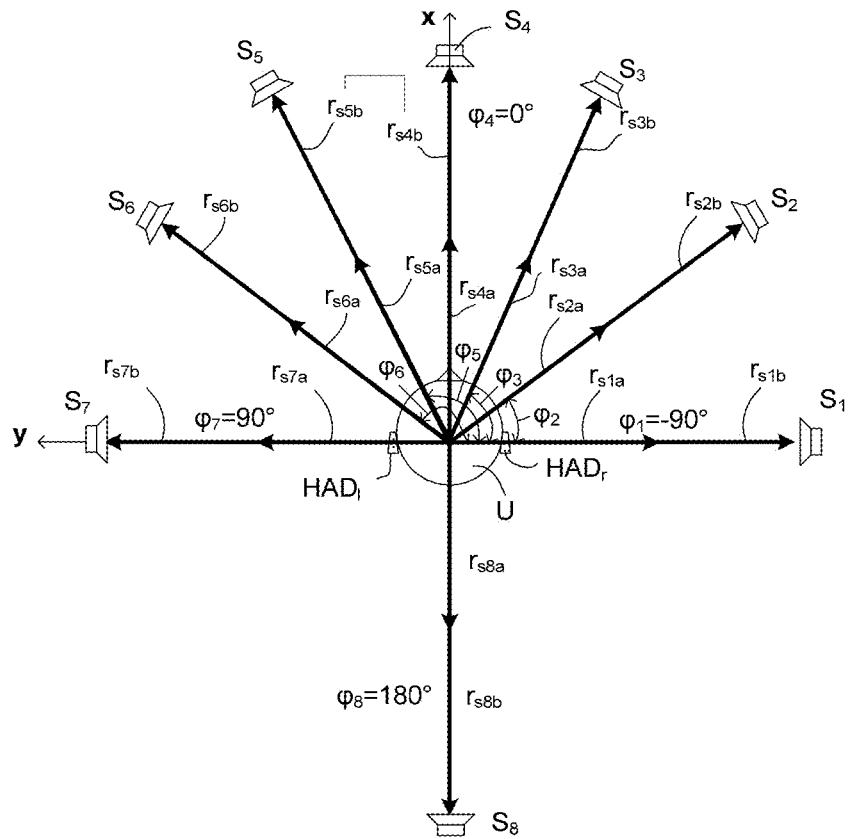

To determine a look vector for a location of a target sound source relative to a user defined by vector $r_{xsrc}$ in FIG. 3A (during normal use of the hearing assistance device), one approach could be to compare the front look vector $d_{cal}$ determined for distance $r_{cal}$ based on the available calibration signal (according to the present disclosure) by comparison with the front look vectors stored in memory ($d_{pd}(\phi$, |r|,person). If/when a close match is found for a front look vector for a given person-type, the look vector corresponding to $\phi$, |r| (e.g. 30°, 2 m) of the relevant vector $r_{xsrc}$ as stored in the memory for the given person-type is selected and used as an estimate of the true look vector in the current situation. There exist a range of other possible ways of predicting a given look vector based on measurement of another. For example, the new look vector for the desired (angle, range) pair may be estimated from the known look vector in a probabilistic setting. Specifically, the look vectors measured for a given fixed position (angle, range) for different persons, may be modelled as realizations of an M dimensional random variable, e.g., distributed according to an M-dimensional, complex-valued Gaussian distribution. Furthermore, assuming that look vectors measured at different positions are jointly Gaussian, it is possible to find minimum mean-square error, maximum a posteriori, or maximum likelihood estimates of the unknown look vector.

2B. Reverberant Robust Method Using Click Train Excitation

As detailed above, the external device emits an acoustic calibration signal, and the hearing assistance device(s) estimate the inter-microphone covariance matrix $R_{ss}(k)$ and subsequently the look vector d(k) based on the resulting microphone signals. Ideally, this calibration is performed in a reverberant-free environment, but peoples' homes are generally reverberant. Therefore, a calibration method, which is robust to reverberation is of interest. Such a method could be devised when using a click train as calibration signal. To avoid that the estimate of $R_{ss}(k)$ is "polluted" by reflections, the estimate may be based on time regions immediately after a click is emitted, such that the wavefront impinging on the microphones is included when estimating $R_{ss}(k)$ but such that any possible reflections of this wavefront is not. The procedure is illustrated in FIG. 4. That is, the summation used in $$\hat{R}_{ss}(k) = \frac{1}{N} \sum_n s(n,k) s^H(n,k)$$

would be across time regions ($\Delta T_M$ in FIG. 4C) immediately after the emission of each click (Click in FIG. 4C) in a click train, e.g., in the time duration of [0; 6 ms], while later time points are excluded. Using a click train (comprising a multitude $N_{TRAIN}$ of individual click pulses (indicated by the three click pulses (Click) separated by the broken time line, symbolising the option of an arbitrary number of clicks) would allow to have sufficiently many terms in the sum to achieve a reliable estimate of $R_{ss}(k)$. Preferably, the distance in time between successive clicks is larger than the reverberation time (e.g. parameter T60) of the specific acoustic environment of the measurements. In an embodiment, the total measurement time $T_M$ is adapted to the current background noise level.

Figure 4A:
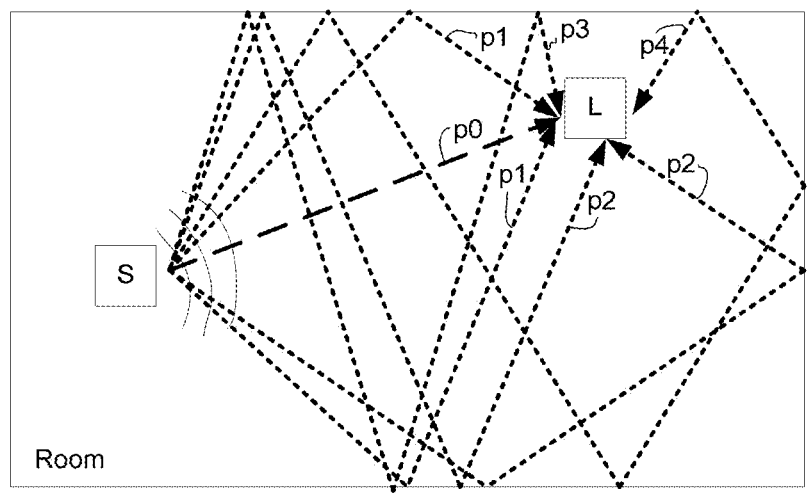
Figure 4B:
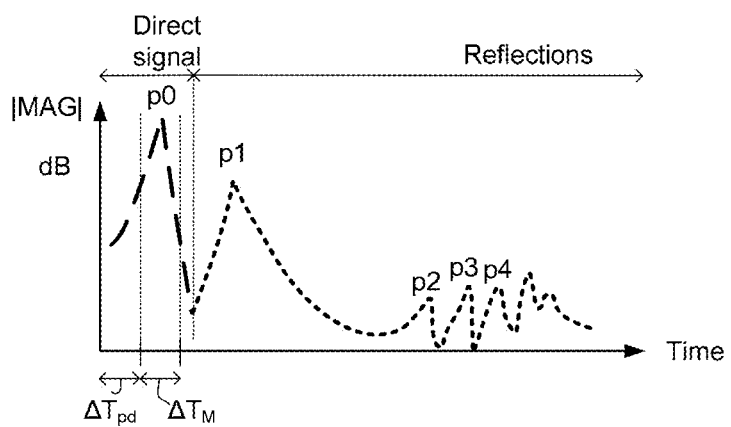
Figure 4C:
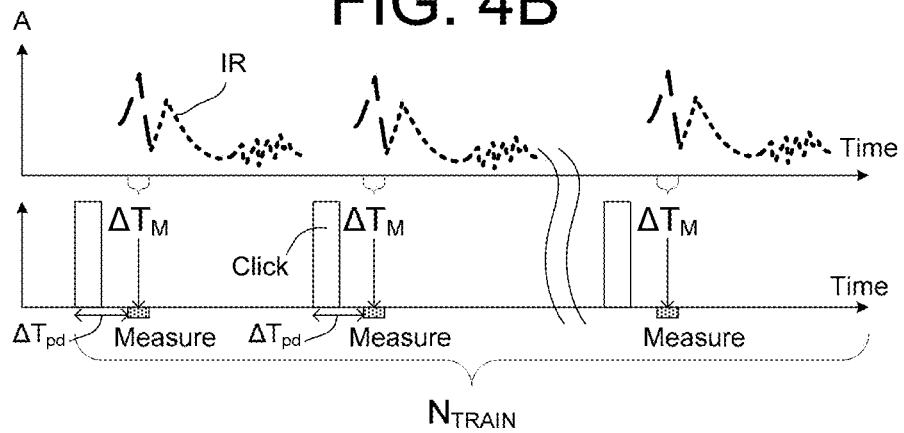

FIG. 4A schematically shows an example of an acoustically propagated signal from an audio source (S in FIG. 4A) to a listener (L in FIG. 4A) via direct ($p_0$) and reflected propagation paths ($p_1$, $p_2$, $p_3$, $p_4$, respectively) in an exemplary location (Room). The resulting acoustically propagated signal received by a listener, e.g. via a hearing assistance device worn by the listener (at L in FIG. 4A) is a sum of the five (and possibly more, depending on the room) differently delayed and attenuated (and possibly otherwise distorted) contributions. The direct ($p_0$) propagation path is indicated FIG. 4a in dashed line, whereas the 'reflections' (here the 1, 2, 3, and 4 times reflected ($p_1$, $p_2$, $p_3$, $p_4$)) are indicated in FIG. 4A in dotted line. FIG. 4B schematically illustrates an example of a resulting time variant sound signal (magnitude |MAG| [dB] versus Time) from the sound source S as received at the listener L (hearing assistance device). The direct part of the signal ($p_0$, dashed part of the graph) appear at the location of the hearing assistance device (@L) $\Delta T_{pd}$ after it was played by the auxiliary device (S). It is assumed that no reflecting surface is closer than the distance from the sound source (S, auxiliary device) to the listener (L, hearing assistance device), so that $p_0 < p_i$, i=1, 2, .... The direct target signal components (dashed part of the graph in FIG. 4B) are separated from the (undesired) reverberation (noise) signal components (dotted part of the graph in FIG. 4B) by a vertical dotted line. The duration and occurrence in time of the direct and reflective parts of the impulse response depend on the location (distance to and properties of reflective surfaces) and the distance between audio source (S) and listener (L), the effect of reverberation being smaller the smaller the distance between source and listener. FIG. 4C illustrates a measurement procedure for calibrating a noise reduction system NRS according to the present disclosure, wherein a calibration signal (TstSo in FIG. 1) in the form of a click pulse (a single- or multi-frequency sound of short duration, as e.g. used in auditory diagnostic measurements, e.g. ABR) or a train of click pulses (Click in FIG. 4C) is played by the loudspeaker (AD-SPK in FIG. 1) of the auxiliary device (AD in FIG. 1). When received by the input units (e.g. MIC in FIG. 1, or $IU_1, \ldots, IU_M$ of FIG. 2) of the hearing assistance device (HAD in FIG. 1, 2), a target covariance matrix $R_{ss}(k)=E[s(m,k)s^H(m,k)]$ is estimated based on the signal components received during a first part ($\Delta T_M$ in FIG. 4c) of the time interval between two successive pulses, where the direct part of the impulse response IR of the click pulse is present in the signals received at the input units (as indicated in the schematic impulse responses IR of the click pulses in the upper part of FIG. 4C, the impulse responses IR being equivalent to the one illustrated and discussed in connection with FIG. 4B). In an embodiment, the measurement time $\Delta T_M$ around the peak of the direct signal part $p_0$ is around 1 ms. In an embodiment, the propagation delay $\Delta T_{pd}$ of the calibration signal from the source to the listener is around 3 ms (corresponding to a distance of approximately 1 m). Preferably, the auxiliary device informs the hearing assistance device about the start time of the calibration signal to allow the hearing assistance device to initiate the measurement period at an appropriate time relative to the arrival of the direct part of the signal. Preferably, the auxiliary device informs the hearing assistance device about characteristics of the calibration signal allowing the hearing assistance device to determine a transfer function from the sound source to the input unit in question (and thus to determine a look vector d).

Figure 5A:
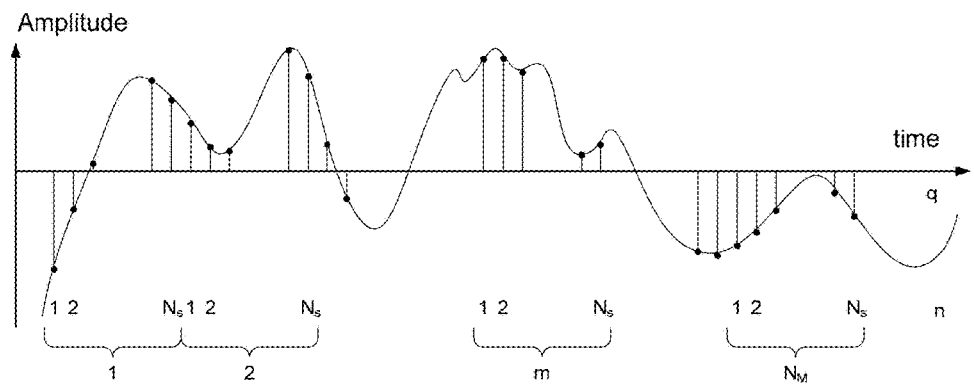
Figure 5B:
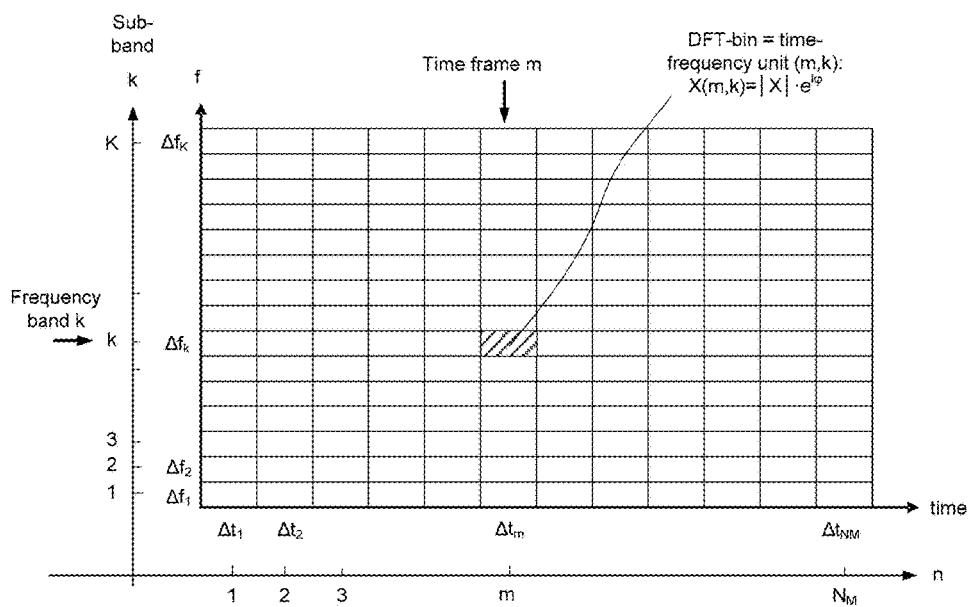

FIG. 5 schematically shows a conversion of a signal in the time domain to the time-frequency domain, FIG. 5a illustrating a time dependent sound signal (amplitude versus time) and its sampling in an analogue to digital converter, FIG. 5b illustrating a resulting 'map' of time-frequency units after a (short-time) Fourier transformation of the sampled signal.

FIG. 5a illustrates a time dependent sound signal x(n) (amplitude versus time (n)), its sampling in an analogue to digital converter and a grouping of time samples in frames, each comprising $N_s$ samples. The graph showing a Amplitude versus time (solid line in FIG. 5A) may e.g. represent the time variant analogue electric signal provided by an input transducer, e.g. a microphone, before being digitized by an analogue to digital conversion unit. FIG. 5B illustrates a 'map' of time-frequency units resulting from a Fourier transformation (e.g. a discrete Fourier transform, DFT) of the input signal of FIG. 5A, where a given time-frequency unit (m,k) corresponds to one DFT-bin and comprises a complex value of the signal X(m,k) in question ($X(m,k)=|X| \cdot e^{i\phi}$, $|X|$=magnitude and $\phi$=phase) in a given time frame m and frequency band k. In the following, a given frequency band is assumed to contain one (generally complex) value of the signal in each time frame. It may alternatively comprise more than one value. The terms 'frequency range' and 'frequency band' are used in the present disclosure. A frequency range may comprise one or more frequency bands. The Time-frequency map of FIG. 5B illustrates time frequency units (m,k) for k=1, 2, . . . , K frequency bands and m=1, 2, . . . , $N_M$ time units. Each frequency band $\Delta f_k$ is indicated in FIG. 5B to be of uniform width. This need not be the case though. The frequency bands may be of different width (or alternatively, frequency channels may be defined which contain a different number of uniform frequency bands, e.g. the number of frequency bands of a given frequency channel increasing with increasing frequency, the lowest frequency channel(s) comprising e.g. a single frequency band). The time intervals $\Delta t_m$ (time unit) of the individual time-frequency bins are indicated in FIG. 5B to be of equal size. This need not be the case though, although it is assumed in the present embodiments. A time unit $\Delta t_m$ is typically equal to the number $N_s$ of samples in a time frame (cf. FIG. 5A) times the length in time $t_s$ of a sample ($t_s=(1/f_s)$, where $f_s$ is a sampling frequency). A time unit is e.g. of the order of ms in an audio processing system.

Figure 6A:
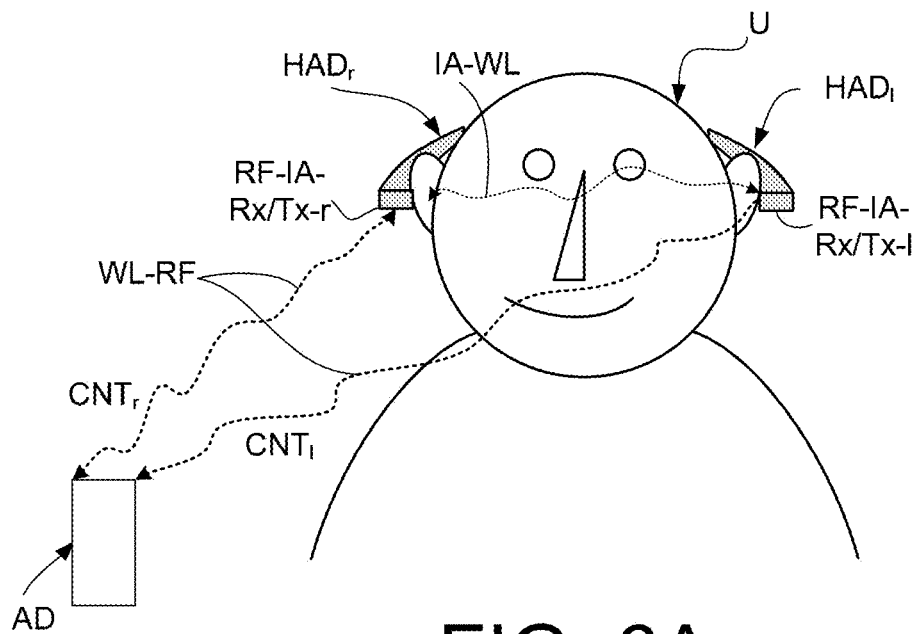
FIG. 6 shows an exemplary application scenario of an embodiment of a hearing assistance system according to the present disclosure, FIG. 6A illustrating a user, a binaural hearing aid system and an auxiliary device during a calibration procedure of the noise reduction system, and FIG. 6B illustrating the auxiliary device running an APP for initiating the calibration procedure.
Figure 6B:
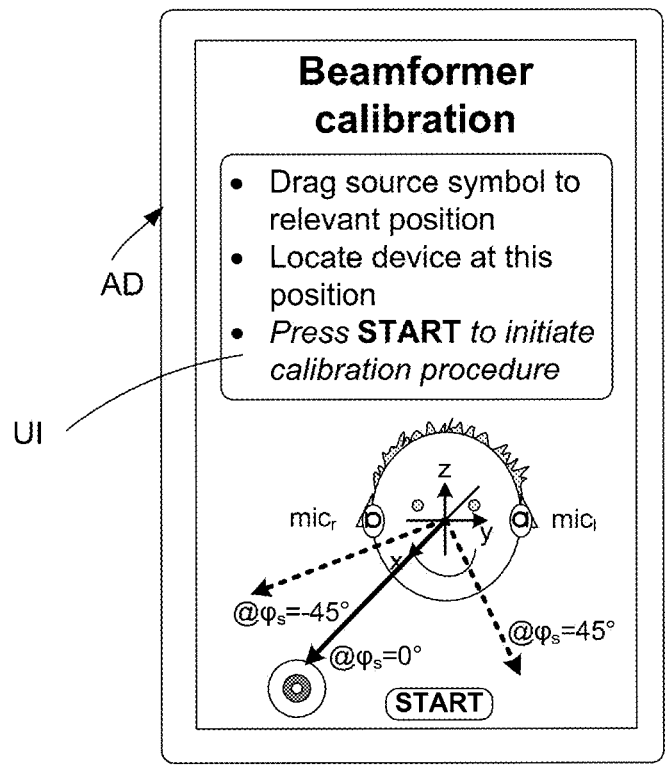

FIG. 6 shows an exemplary application scenario of an embodiment of a hearing assistance system according to the present disclosure, FIG. 6A illustrating a user, a binaural hearing aid system and an auxiliary device during a calibration procedure of the noise reduction system, and FIG. 6B illustrating the auxiliary device running an APP for initiating the calibration procedure.

FIG. 6A shows an embodiment of a binaural hearing aid system comprising left (second) and right (first) hearing assistance devices ($HAD_l$, $HAD_r$) in communication with a portable (handheld) auxiliary device (AD) functioning as a user interface (UI) for the binaural hearing aid system. In an embodiment, the binaural hearing aid system comprises the auxiliary device AD (and the user interface UI). The user interface UI of the auxiliary device AD is shown in FIG. 6B. The user interface comprises a display (e.g. a touch sensitive display) displaying a user of the hearing assistance system and a number of predefined locations of the calibration sound source relative to the user. Via the display of the user interface (under the heading Beamformer calibration), the user U is instructed to Drag source symbol to relevant position
Locate device at this position
Press START to initiate calibration procedure
These instructions should prompt the user to
Place the device in a direction relative to the user where the target sound source is expected to be located, e.g. in front of the user.
Preferably, the device should be at level with the eyes (and ears) of the user.
Press start to initiate calibration procedure.

Hence, the user is encouraged to choose a location for a current calibration sound source by dragging a sound source symbol (circular icon with a grey shaded inner ring) to the approximate location of the calibration sound source (if deviating from a front direction). The 'Beamformer calibration' is e.g. implemented as an APP of the auxiliary device AD (e.g. a SmartPhone). Preferably, the initiation (start time of calibration signal) of the calibration procedure (pressing of START), the chosen location (e.g. angle and distance to the user), and possibly characteristics of the calibration signal (magnitude vs. frequency, number and time distance between of calibration pulses, etc.), are communicated to the left and right hearing assistance devices for use in choosing an appropriate corresponding predetermined set of filter weights, or for calculating such weights based on the received data and the calibration signal. In the embodiment of FIG. 6, the auxiliary device AD comprising the user interface UI is adapted for being held in a hand of a user (U), and hence convenient for displaying a current location of a target sound source. Alternatively, the auxiliary device may form part of a fitting system and be placed at predefined locations relative to the user. The calibration procedure may e.g. be controlled via the fitting system (the fitting system e.g. comprising a computer and fitting software running on the computer).

Figure 7:
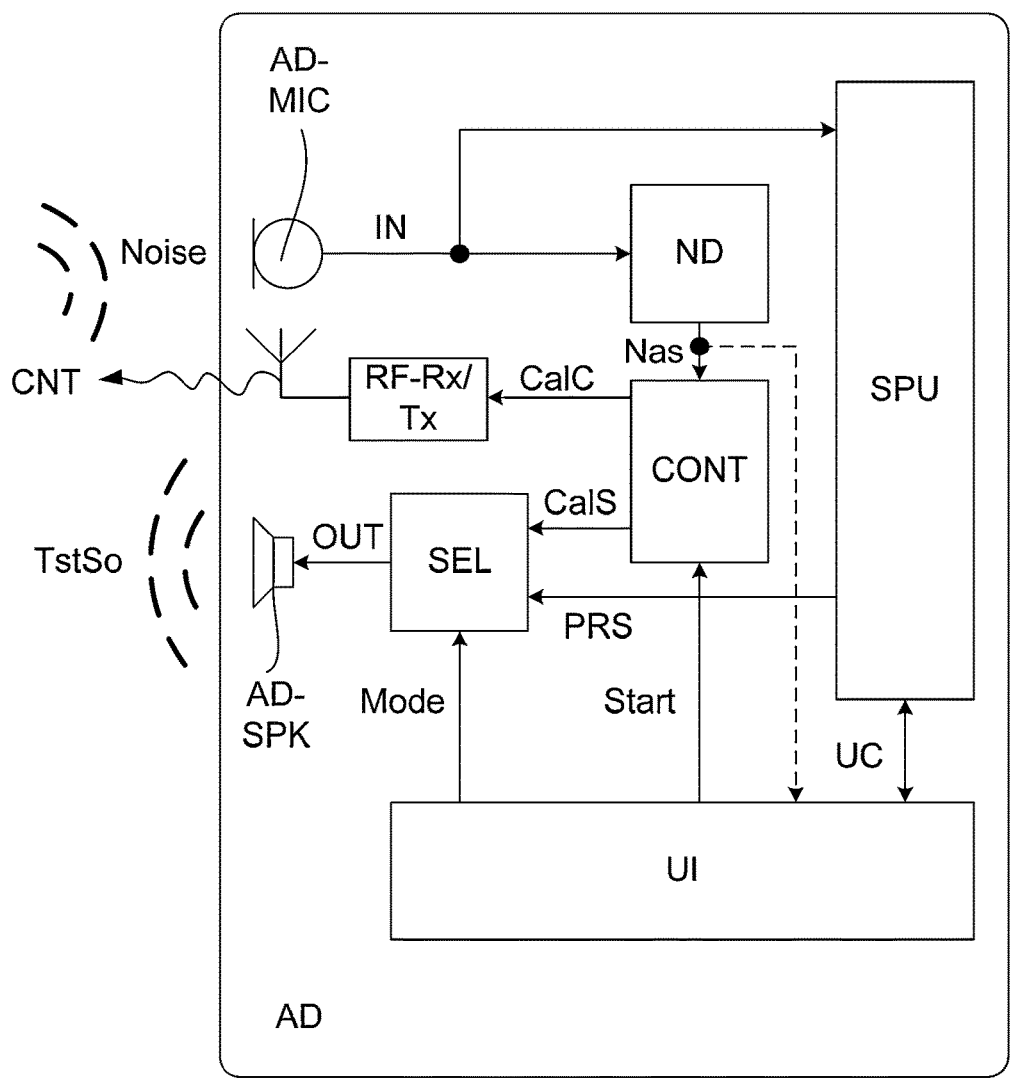
FIG. 7 shows an embodiment of an auxiliary device according to the present disclosure.

FIG. 7 shows an embodiment of an auxiliary device AD according to the present disclosure. The auxiliary device AD comprises a microphone (AD-MIC) for picking up a sound signal from the environment, e.g. a noise signal (Noise) during or prior to a calibration procedure. The sound signal is converted to an electric input signal IN, which is communicated to a signal processing unit (SPU) and to a noise detector (ND) for monitoring the (noise) input signal IN (e.g. detecting a level and/or analysing a frequency content, etc.). A resulting noise analysis signal Nas (e.g. indicative of its level or frequency spectrum) is communicated to a control unit (CONT) for controlling the calibration procedure, including generating a calibration signal CalS (possibly shaped in frequency, e.g. modified in level and/or duration in time dependent on the noise analysis signal Nas). The (electric) calibration signal CalS is converted to a calibration sound signal TstSo by loudspeaker (AD-SPK). The control unit (CONT) receives a signal (Start) from the user interface (UI) indicating that the user has activated the START 'button' (cf. FIG. 6B), which initiates the calibration procedure. Prompted by the Start signal, the control unit (CONT) generates calibration control signal CalC, which is transmitted to the hearing assistance device(s) (e.g. $HAD_l$, $HAD_r$ in FIG. 6A) via transceiver and antenna circuitry (RF-Rx/Tx, ANT, signal CNT, and wireless link WL-RF). The activation of the START 'button' via user interface UI (see FIG. 6B) brings the auxiliary device (from a NORMAL mode) into a CALIBRATION mode and generates control signals Mode to selection unit (SEL), Start to control unit (CONT), and UC to signal processing unit (SPU). The Mode signal controls the selector (SEL) selecting calibration signal CalS as output signal OUT (input signal to the loudspeaker, AD-SPK), when the CALIBRATION mode is activated, and the normal processed signal PRS from the signal processing unit (SPU), when the NORMAL mode is activated. The control signal UC may inhibit the normal processing in the signal processing unit (SPU) when the CALIBRATION mode is activated. Further, the control signal UC may carry information data intended for being presented to the user from the signal processing unit (SPU) to the user interface (UI). In an embodiment, the user is informed about the result of the analysis of the noise analysis, e.g. if a noise level is above a noise level threshold via the user interface (cf. dashed signal Nas in FIG. 7 from noise detector ND to user interface UI). Thereby, the user may be discouraged from executing the calibration procedure while a noise level is too high.

In an embodiment, communication between the hearing assistance device and the auxiliary device is in the base band (audio frequency range, e.g. between 0 and 20 kHz). Preferably however, communication between the hearing assistance device and the auxiliary device is based on some sort of modulation at frequencies above 100 kHz. Preferably, frequencies used to establish a communication link between the hearing assistance device and the auxiliary device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology) or a related technology.

In the embodiment of FIG. 6a, wireless links denoted IA-WL (e.g. an inductive link between the hearing left and right assistance devices) and WL-RF (e.g. RF-links (e.g. Bluetooth) between the auxiliary device AD and the left $HAD_l$, and between the auxiliary device AD and the right $HAD_r$, hearing assistance device, respectively) are indicated (implemented in the devices by corresponding antenna and transceiver circuitry, indicated in FIG. 6a in the left and right hearing assistance devices as RF-IA-Rx/Tx-l and RF-IA-Rx/Tx-r, respectively).

In an embodiment, the auxiliary device AD is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s). In an embodiment, the function of a remote control is implemented in a SmartPhone, the SmartPhone possibly running an APP allowing to control the functionality of the audio processing device via the SmartPhone (the hearing assistance device(s) comprising an appropriate wireless interface to the SmartPhone, e.g. based on Bluetooth or some other standardized or proprietary scheme).

In the present context, a SmartPhone, may comprise
- a (A) cellular telephone comprising a microphone, a speaker, and a (wireless) interface to the public switched telephone network (PSTN) COMBINED with
- a (B) personal computer comprising a processor, a memory, an operative system (OS), a user interface (e.g. a keyboard and display, e.g. integrated in a touch sensitive display) and a wireless data interface (including a Web-browser), allowing a user to download and execute application programs (APPs) implementing specific functional features (e.g. displaying information retrieved from the Internet, remotely controlling another device, combining information from various sensors of the smartphone (e.g. camera, scanner, GPS, microphone, etc.) and/or external sensors to provide special features, etc.).

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof.

REFERENCES

[Kjems&Jensen; 2012] U. Kjems, J. Jensen, "Maximum likelihood based noise covariance matrix estimation for multi-microphone speech enhancement", 20th European Signal Processing Conference (EUSIPCO 2012), pp. 295-299, 2012.

US2011026725A1 (BERNAFON)

The invention claimed is:

1. A hearing assistance system comprising a hearing assistance device and
an auxiliary device;
the hearing assistance device comprising
HD-a) a multitude M of input units $IU_i$, i=1, ..., M, adapted to provide or to receive a time-frequency representation $S_i(k,m)$ of a signal $s_i(n)$ at an $i^{th}$ input unit in a number of frequency bands and a number of time instances, k being a frequency band index, m being a time index, n representing time, and M being larger than or equal to two; and
HD-b) a multi-input unit noise reduction system comprising a multi-channel beamformer filtering unit operationally coupled to said multitude of input units $IU_i$, i=1, ..., M, and configured to determine filter weights w(k,m) for providing a beamformed signal Y(k,m), wherein signal components from other directions than a direction of a target signal source are attenuated, whereas signal components from the direction of the target signal source are left un-attenuated or are attenuated less than signal components from said other directions;
the system comprising a user interface for activating a calibration mode in the auxiliary device and in the hearing assistance device;
the auxiliary device comprising
AD-a) an output transducer for converting an electric signal representative of a sound to an acoustic sound signal;
AD-b) a control unit for forwarding an electric calibration signal to the output transducer when said calibration mode is activated;
wherein the system, during said calibration mode, is configured to estimate a look vector d(k,m) for a target signal originating from a target signal source located at a specific location relative to the user based on the electric calibration signal converted by the output transducer of the auxiliary device to an acoustic calibration sound signal, the estimated look vector d(k,m) being used to determine optimal beamformer weights, and
wherein said specific location relative to the user is the location of said output transducer of the auxiliary device, wherein said look vector d(k, m) is an M-dimensional vector comprising elements (i=1, ..., M), the $i^{th}$ element d(k,m) defining an acoustic transfer function from the target signal source to the $i^{th}$ input unit, or a relative acoustic transfer function from the $i^{th}$ input unit to a reference input unit.

2. A hearing assistance system according to claim 1 wherein said auxiliary device comprises said user interface for activating the calibration mode.

3. A hearing assistance system according to claim 1 wherein said hearing assistance device and said auxiliary device are adapted to establish a wireless link between them.

4. A hearing assistance system according to claim 3 adapted to communicate one or more of the start time of the calibration signal, the specific location of the auxiliary device relative to the user, and characteristics of the calibration signal to the hearing assistance device.

5. A hearing assistance system according to claim 1 configured to determine filter weights for one or more fixed beamformers based on said estimate of a look vector d(k,m).

6. A hearing assistance system according to claim 5 wherein said fixed beamformers comprise:

an enhanced omni beamformer for providing a beamformed signal $E_{omni}(k,m)$ with a gain of 0 dB when a signal is received from the target direction/location, and/or
a target cancelling beamformer for providing a target-cancelling beamformed signal $C_R(k,m)$, which rejects a signal played from the target direction/location.

7. A hearing assistance system according to claim 5 wherein the fixed beamformer(s) is/are determined from the estimated look vector $\widehat{d(k,m)}$ and an estimate of the inter-input unit covariance matrix $\hat{R}_{vv}(k,m)$ of the noise $v_i$ impinging on the respective input units (i=1, 2, ..., M).

8. A hearing assistance system according to claim 7 wherein an estimate of the noise covariance matrix, termed $\hat{R}_{vv,diffuse}(k, m)$, is predetermined and stored in a memory of the hearing assistance device.

9. A hearing assistance system according to claim 1 configured to determine filter weights for one or more fixed beamformers based an assumption of the spatial noise distribution.

10. A hearing assistance system according to claim 1 wherein said hearing assistance device further comprises a single channel post-processing filter unit operationally coupled to said multi-channel beamformer filtering unit and configured to provide an enhanced signal $\hat{S}(k, m)$.

11. A hearing assistance system according to claim 1 comprising a control unit configured to compare beamformer weights $w_{cal}(k,m)$ resulting from the calibration to a set of default beamformer weights $w_{pd}(k,m)$ and to provide a difference measure.

12. A hearing assistance system according to claim 11 adapted to provide that default beamformer weights are used, if the difference measure is above a predefined threshold.

13. A hearing assistance system according to claim 1 configured to provide that the calibration signal is adapted to the current noise level and/or spectrum, by shaping the calibration signal to ensure a predetermined calibration signal to noise ratio and/or the duration in time of the calibration signal.

14. A hearing assistance system according to claim 1 comprising a voice activity detector for estimating whether or not a target signal is present or dominating at a given point in time.

15. A hearing assistance system according to claim 1 wherein the auxiliary device comprises, a remote control, an audio gateway device, a mobile telephone, or a computer.

16. A hearing assistance system according to claim 1 wherein the auxiliary device comprises or forms part of a fitting system.

17. A hearing assistance system according to claim 1 comprising a sensor for allowing a user a) to locate the auxiliary device at a predetermined angle and/or height and/or distance relative to the user and/or b) to track the location of the auxiliary device relative to the user.

18. A hearing assistance system according to claim 1 wherein the hearing assistance device comprises a hearing instrument adapted for being located at the ear or fully or partially in the ear canal of a user, or for being fully or partially implanted in the head of a user, a headset, an earphone, an ear protection device or a combination thereof.

19. A method of calibrating a multi-input unit noise reduction system of a hearing assistance device, the method comprising:

providing a hearing assistance device comprising the multi-input unit noise reduction system and a multitude M of input units, where M is larger than or equal to two;

providing an auxiliary device comprising an output transducer;

locating the auxiliary device within a predetermined distance of a user wearing said hearing assistance device, thereby defining a specific location of (the output transducer of) the auxiliary device relative to (the hearing assistance device of) the user;

initiating a calibration mode in the hearing assistance device and the auxiliary device;

providing an acoustic calibration signal by the output transducer of the auxiliary device;

providing a time-frequency representation $S_i(k,m)$ of the calibration signal $s_i(n)$ at an $i^{th}$ input unit, $i=1, 2, \ldots, M$, in a number of frequency bands and a number of time instances, k being a frequency band index and m being a time index, the method further comprising:

estimating a look vector $d(k, m)$ for a target signal originating from a target signal source located in said specific location relative to the user based on said time-frequency representation $S_i(k,m)$ of the calibration signal $s_i(n)$, $i=1, 2, \ldots, M$, wherein said look vector $d(k,m)$ is an M-dimensional vector comprising elements ($i=1, \ldots, M$), the $i^{th}$ element $d_i(k,m)$ defining an acoustic transfer function from the target signal source to the $i^{th}$ input unit, or a relative acoustic transfer function from the $i^{th}$ input unit to a reference input unit; and determining optimal beam former weights based on said estimated look vector $\widehat{d(k,m)}$.

* * * * *